United States Patent
Fishberger et al.

(10) Patent No.: US 8,985,267 B2
(45) Date of Patent: *Mar. 24, 2015

(54) STETHESCOPE DISPOSABLE COVERS

(71) Applicants: Kenneth I. Fishberger, Setauket, NY (US); David M. Schwartzberg, East Setauket, NY (US)

(72) Inventors: Kenneth I. Fishberger, Setauket, NY (US); David M. Schwartzberg, East Setauket, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/155,757

(22) Filed: Jan. 15, 2014

(65) Prior Publication Data

US 2014/0124287 A1    May 8, 2014

Related U.S. Application Data

(63) Continuation of application No. 13/688,451, filed on Nov. 29, 2012, now Pat. No. 8,662,244.

(60) Provisional application No. 61/662,351, filed on Jun. 20, 2012.

(51) Int. Cl.
  *A61B 7/02* (2006.01)
  *A61B 19/02* (2006.01)
  *A61B 19/08* (2006.01)

(52) U.S. Cl.
  CPC .............. *A61B 7/02* (2013.01); *A61B 19/026* (2013.01); *A61B 19/0256* (2013.01); *A61B 19/081* (2013.01)
  USPC ........................................................ 181/131

(58) Field of Classification Search
  USPC ..................................................... 181/131
  See application file for complete search history.

(56) References Cited

U.S. PATENT DOCUMENTS

| | | |
|---|---|---|
| 5,269,314 A | 12/1993 | Kendall et al. |
| 5,424,495 A | 6/1995 | Wurzburger |
| 5,428,193 A | 6/1995 | Mandiberg |
| 5,448,028 A | 9/1995 | Filion et al. |
| 5,528,004 A | 6/1996 | Wurzburger |
| 5,564,431 A | 10/1996 | Seward |
| 5,686,706 A | 11/1997 | Wurzburger |
| 5,747,751 A | 5/1998 | Weckerle et al. |
| 5,808,244 A * | 9/1998 | Knight et al. ................ 181/131 |
| 5,921,941 A | 7/1999 | Longobardo et al. |
| 5,949,032 A | 9/1999 | Wurzburger |
| 6,009,971 A * | 1/2000 | Weidman et al. ............ 181/131 |
| 6,206,134 B1 | 3/2001 | Stark et al. |
| 6,467,568 B1 | 10/2002 | Kemper |
| 7,469,769 B1 | 12/2008 | Hmayakyan et al. |
| 7,614,478 B2 | 11/2009 | Hmayakyan et al. |
| 7,743,876 B2 * | 6/2010 | Weidman ...................... 181/131 |
| 7,823,690 B2 | 11/2010 | Hirsch et al. |
| 7,882,927 B2 | 2/2011 | Hmayakyan et al. |
| 7,891,462 B2 | 2/2011 | Hmayakyan et al. |
| 8,042,646 B2 | 10/2011 | Gross |
| 8,662,244 B2 * | 3/2014 | Fishberger et al. .......... 181/131 |

* cited by examiner

*Primary Examiner* — Forrest M Phillips
(74) *Attorney, Agent, or Firm* — Sorell, Lenna & Schmidt, LLP

(57) ABSTRACT

A cover for a stethoscope having a head and a diaphragm is provided. The cover includes a first region having first and second sides, and a second region configured to be continuous with the first region and including a crimpable material to form-fit around at least the head of the stethoscope so as to cover the head of the stethoscope from contamination. The first side includes adherent material for removably adhering the first region to the diaphragm of the stethoscope and the second side includes an antimicrobial layer including an antimicrobial substance that can neutralize or destroy microbes disposed thereon.

20 Claims, 5 Drawing Sheets

STETHESCOPE DISPOSABLE COVERS

This application is a continuation of U.S. patent application Ser. No. 13/688,451, filed Nov. 29, 2012, which claims priority to U.S. Provisional Application No. 61/662,351, filed Jun. 20, 2012. Each of the referenced applications is incorporated herein by reference, in its entirety.

BACKGROUND

The present invention relates to a cover for the head and diaphragm of a stethoscope and a system for storing and dispensing covers for stethoscopes.

A stethoscope is an acoustic medical device typically used by a physician or medical care provider to monitor sounds in a patient's organs and/or pathways (respiratory, cardiac, arterial, etc.). Stethoscopes typically include a chest piece for placement against the patient for sensing relatively high frequency sound, an air-filled hollow tube to transmit the sound from the chest piece, and ear tubes to receive the sound from the air-filled hollow tube and transmit the sound via ear tips to the physician or medical care provider. The chest piece is generally known to include a head and a diaphragm which is the part of the chest piece placed against the patient. When the diaphragm is placed on the patient, bodily sounds vibrate the diaphragm creating acoustic pressure sound waves which travel up the air-filled hollow tube and ear tubes to the listener's ears. The physician or medical care provider may then be better able to diagnose a condition or whether the patient's organs or pathways are functioning normally.

In use, stethoscopes and in particular the head and diaphragm of a stethoscope can easily be contaminated with bacteria and other contaminants as stethoscopes are typically used on several patients within an hour. Physicians or medical care providers in a hospital setting see about 20-30 patients an hour including neonatal and pediatric patients, surgery patients, cancer and infectious disease patients and examine these patients using the same stethoscope. Medical providers typically employ a stethoscope on most of the patients they see in a hospital setting and anywhere between 6-12 patients per hour in an office setting. Transmission of bacterial infections among patients, particularly in a hospital setting, has become a huge concern especially in view of the development of antibiotic-resistant strains of staphylococcal infections and other resistant strains of bacteria, Viruses, and Fungal infections. Examples of resistant strains of bacteria include but are limited to, vancomycin resistant enterococcus and clostridium dificile; Viruses—Hepatitis B and C; and Fungal infections such as *Aspergillosis, Candida*. Accordingly, the use of protective covers for stethoscopes has become increasingly important.

Protective covers for stethoscopes are well known. Typical covers include a thin sheet of plastic having an adhesive backing which can be applied over the diaphragm of a stethoscope before use on each new patient. After use, the cover is typically removed and discarded. These covers can function adequately, however, too often do problems arise with the use of such covers. Such problems include the cover falling off the stethoscope during application, the cover not fitting with an air-tight seal on the diaphragm during application, poor acoustic transmission and the transmission of microorganisms, fluids or other contaminants to the head of the stethoscope and in some cases, the diaphragm of the stethoscope. Most often the design is cumbersome and takes too much time to deploy Accordingly, a need exists for a cover for the head and diaphragm of a stethoscope that will securely fit onto the head and diaphragm, can be easily applied to the diaphragm to form a substantially air-tight seal without any air bubbles or wrinkling of the cover, is acoustically transmissive and protects against the transmission of microorganisms and fluids. It is imperative that the stethoscope cover be designed so that it is easy and quick to deploy since the time that a medical provider has with a patient is limited. Further, there is a need for an inexpensive system for efficiently dispensing covers for physicians and medical care providers.

SUMMARY

New covers for stethoscopes that securely fit onto the head and diaphragm of a stethoscope, can be quickly adhered to stethoscopes with a substantially air-tight seal without any air bubbles or wrinkling of the cover, prevent cross-contamination from patient to patient and are acoustically transmissive are provided. One embodiment of a cover for a stethoscope having a head and a diaphragm provides for a cover including a first region having first and second sides, and a second region configured to be continuous with the first region and including a crimpable material to form-fit around at least the head of the stethoscope so as to cover the head of the stethoscope from any contamination. The first region is acoustically transmissive and substantially impermeable to microorganisms and fluids. The first side of the first region includes an adherent material for removably adhering the first region to the diaphragm of the stethoscope. The second side of the first region includes an antimicrobial layer having an antimicrobial substance that can neutralize or destroy microbes disposed thereon as well as at a site on a patient where the diaphragm is applied. The antimicrobial substance can be at least partially removable so that at least a portion of the antimicrobial substance is left behind as the cover is removed from the stethoscope for disposal. The first region can further include at least one tab extending outwardly having a first side opposite the first side of the first region that includes an adherent material and is configured to wrap around at least a portion of the head of the stethoscope to further secure the cover to the stethoscope. In some embodiments, the first region has a thickness in the range of from about 0.1 mm to about 0.4 mm.

In another embodiment of a cover for a stethoscope having a head and a diaphragm, a cover is provided including a first layer including an adherent material for removably adhering the cover to the diaphragm and the head of the stethoscope, and a second layer including a crimpable material to form-fit the cover around at least the diaphragm and the head of the stethoscope so as to form a protective barrier between a patient and the stethoscope. The first and second layers are acoustically transmissive and substantially impermeable to microorganisms and fluids. The first layer and/or second layer can further include an antimicrobial substance that can neutralize or destroy microbes disposed therein. In some embodiments, the first layer has a thickness in the range of from about 0.1 mm to about 0.4 mm.

A system for storing and dispensing at least one cover for a stethoscope having a head and a diaphragm is also provided. The system includes an enclosure having at least one opening and a plurality of covers removably attached to the enclosure. The covers include a first region having first and second sides, and a second region configured to be continuous with the first region and including a crimpable material to form-fit around at least the head of the stethoscope and protect against any contamination. The first region is acoustically transmissive and substantially impermeable to microorganisms and fluids.

The first side of the first region includes an adherent material for removably adhering the first region to the diaphragm of the stethoscope. The second side of the first region includes an antimicrobial layer having an antimicrobial substance that can neutralize or destroy microbes disposed thereon. The enclosure can further include an antimicrobial ultraviolet light source and/or a container for catching the backing after a stethoscope cover is removed from the backing.

In some embodiments, the system further includes a bracket to mount the enclosure on a wall and a port for replenishing stethoscope covers configured to receive a plurality of stethoscope covers. The port can further include a roller mechanism configured to hold a plurality of stethoscope covers removably disposed on a releasable backing and wound about a roller so that as a stethoscope cover is dispensed from the backing the roller advances to expose the next available stethoscope cover.

In various embodiments, the cover forms a substantially air-tight seal with the diaphragm without any air bubbles or wrinkling when the cover is removably adhered to the diaphragm. In some embodiments, the cover can be shaped as a circle, rectangle, octagon, trapezoid, triangle, square or other polygon that is greater than the size of the head of the stethoscope.

In various embodiments, the adherent material includes one or more of a cellophane, vinyl, acetate, polyethylene acrylic, butyl rubber, ethylene-vinyl acetate, natural rubber, a nitrile, silicone rubber, a styrene block copolymer, a vinyl ether and a tackifier. In some embodiments, the adherent material can further include an antimicrobial and/or antiseptic material.

In various embodiments, the crimpable material includes one or more of polyvinyl chloride, polyvinylidene chloride, low density polyethylene, linear low density polyethylene, polyisobutene, poly[ethylene-vinylacetate] copolymer and lightweight aluminum foil. In some embodiments, the crimpable material can further include an adhesive material so as to enhance adhesion of the crimpable material to itself so as to secure the cover to the stethoscope.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties that are sought by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a handle" includes one, two, three or more handles.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

Figure 1:
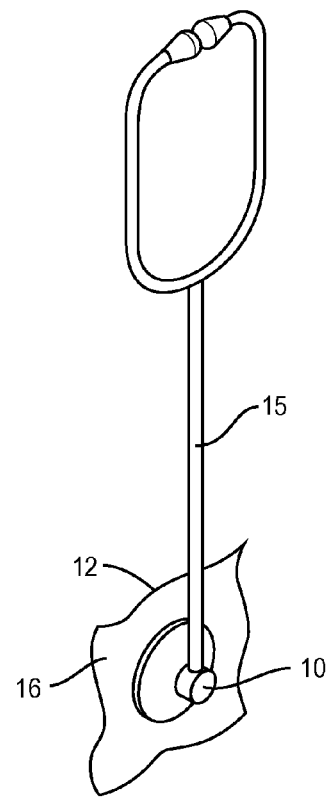
FIG. 1 is a perspective view of a cover adhered onto the diaphragm of a stethoscope according to an exemplary embodiment of the present invention.

FIG. 1 is a perspective view of one embodiment of a cover 12 adhered onto the diaphragm (not shown) of a stethoscope 15 via a first region (not shown). Before use of the stethoscope 15 with the cover 12, the second region 16 of the cover 12 is folded and crimped to cover the diaphragm (not shown) and head 10 of the stethoscope 15. Covering the head 10 by crimping the cover over the diaphragm protects the head 10 from microbes released from the patient's while being examined. The configuration and the material of which the stethoscope cover is made allow the covers to be quickly and easily applied to the head and diaphragm of the stethoscope prior to examination of a patient.

Figure 2:
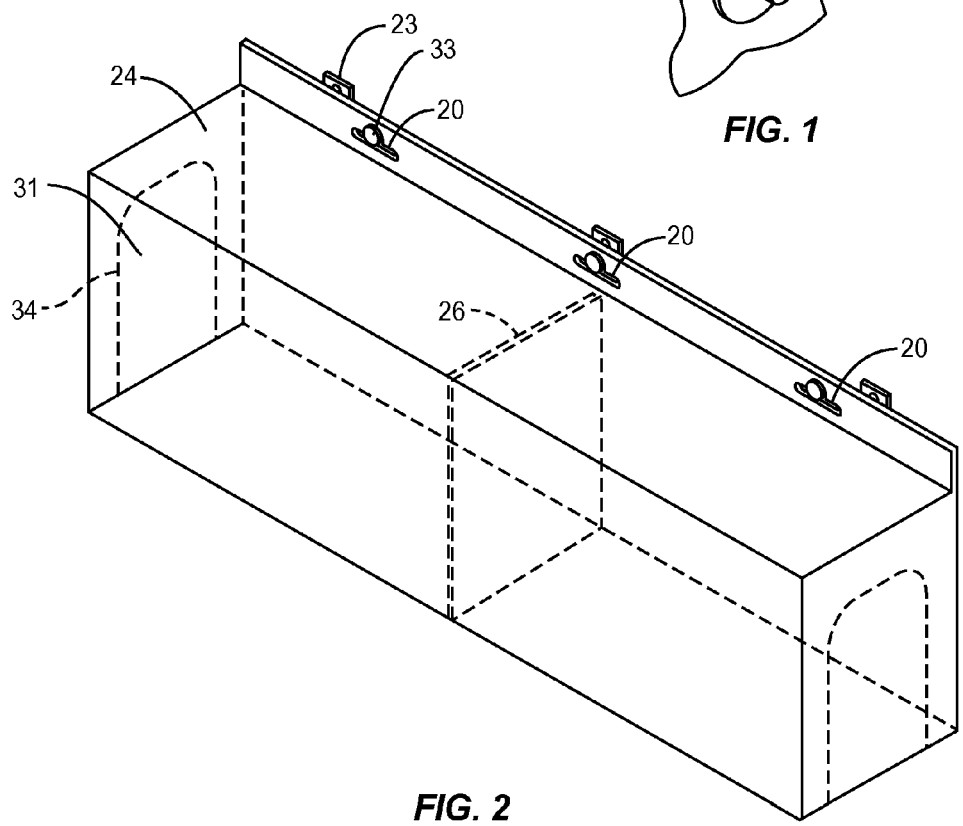
FIG. 2 is a perspective view of a system for storing and dispensing stethoscope covers.

FIG. 2 is a perspective view of a system for storing and dispensing stethoscope covers including an enclosure 24 and a plurality of covers (not shown). The enclosure 24 holds the covers (not shown). The enclosure 24 may be made of a sturdy material, for example, a metal or hard plastic. The enclosure 24 may be mounted onto a wall (not shown) by using a bracket 23. This is further described below and shown in FIG. 3. The enclosure 24 includes two (2) access openings 34 and each access opening 34 encompasses a portion 31. Physicians and/or medical care providers can access covers (not shown) inside the enclosure 24 by tearing away a portion 31 at an access opening 34. The enclosure in FIG. 2 also includes a central plate 26. The central plate 26 can be adhered to the covers (not shown) to provide stability to the plurality of covers (not shown) when the user attempts to retrieve a cover. The central plate 26 may be made of a sturdy material, for example, hard plastic or metal.

Figure 3:
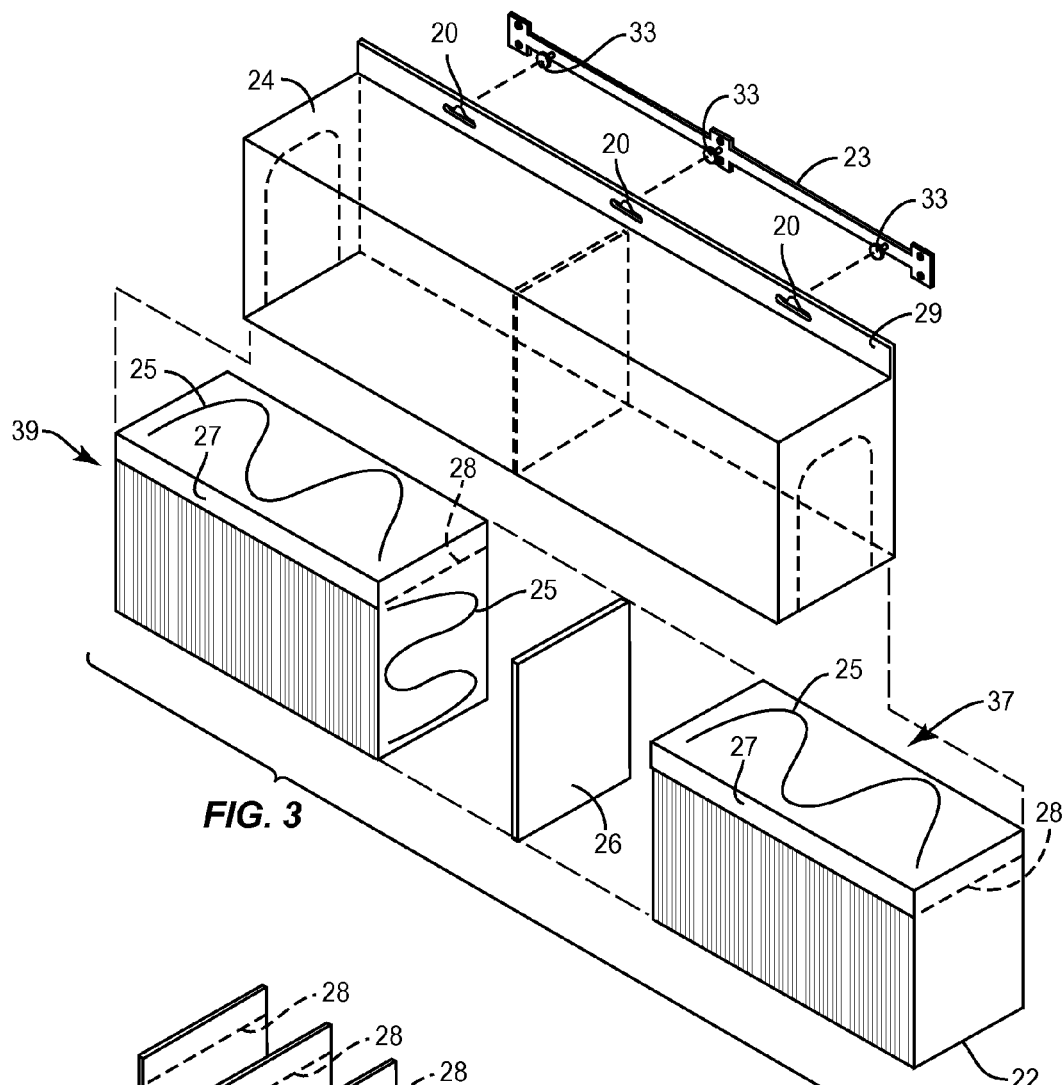
FIG. 3 is an exploded perspective view of the storing and dispensing system of FIG. 2 with stethoscope covers disposed therein.

FIG. 3 is an exploded perspective view of the storing and dispensing system of FIG. 2 with stethoscope covers disposed therein. The enclosure 24 has a flap 29 including orifices 20 to secure the enclosure 24 to hooks 33 on a mounting bracket 23 that can be mounted on a wall (not shown). As further shown in FIG. 3, the enclosure 24 includes a central plate 26 which separates a first block 37 formed by a plurality of covers 22 and a second block 39 formed by a plurality of covers 22. Each of the blocks 37 and 39 are formed by binding together a plurality of covers 22 using a binder 27. The first and second blocks, 37 and 39, are secured to the enclosure 24 by using an adhesive material 25 on the top of the blocks 37 and 39. The adhesive material 25 can be a hot glue, epoxy and non-epoxy based bonding materials, chemical and thermal welding materials as well as other non-toxic bonding materials.

Figure 4:
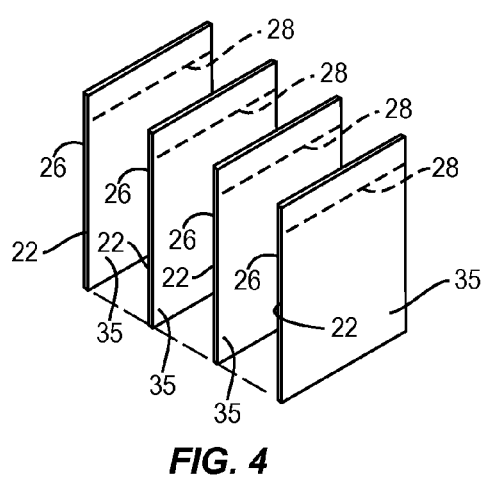
FIG. 4 is an exploded perspective view of the stethoscope covers disposed in the system shown in FIG. 3.

FIG. 4 shows an exploded view of the covers 22 shown in FIG. 3. The covers 22 are disposable and each cover 22 includes a layer of adherent material 35 for removably adhering the cover 22 to the diaphragm and the head of a stethoscope (not shown). The layer of adherent material 35 can include one or more of a cellophane, vinyl, acetate, polyethylene acrylic, butyl rubber, ethylene-vinyl acetate, natural rubber, a nitrile, silicone rubber, a styrene block copolymer, a vinyl ether and a tackifier. In some embodiments, the layer of adherent material 35 is sprayed or coated with a weak adhesive non-toxic glue, for example, spirit gum, when additional adherency is desired.

Each cover 22 in FIG. 4 also includes a layer of a crimpable material 26 to form-fit the cover 22 around at least the diaphragm and the head of a stethoscope (not shown) so as to form a protective barrier between a patient and the stethoscope. The layer of crimpable material 26 also prevents adjacent covers 22 from sticking together. In some embodiments, the layer of crimpable material 26 may be sprayed or coated with a chemical agent made of wax to further prevent adjacent covers 22 from sticking together. Both the layer of adherent material 35 and the layer of crimpable material 26 are acoustically transmissive and substantially impermeable to microorganisms and fluids.

The covers 22 in FIG. 4 also include a perforation line 28 to allow for easy dislodging of the covers 22 from a binding 27.

In use, a medical care provider can quickly tear a cover 22 from the binding 27 at a perforation line 28 by pulling on the cover 22.

Figures 5, 6:
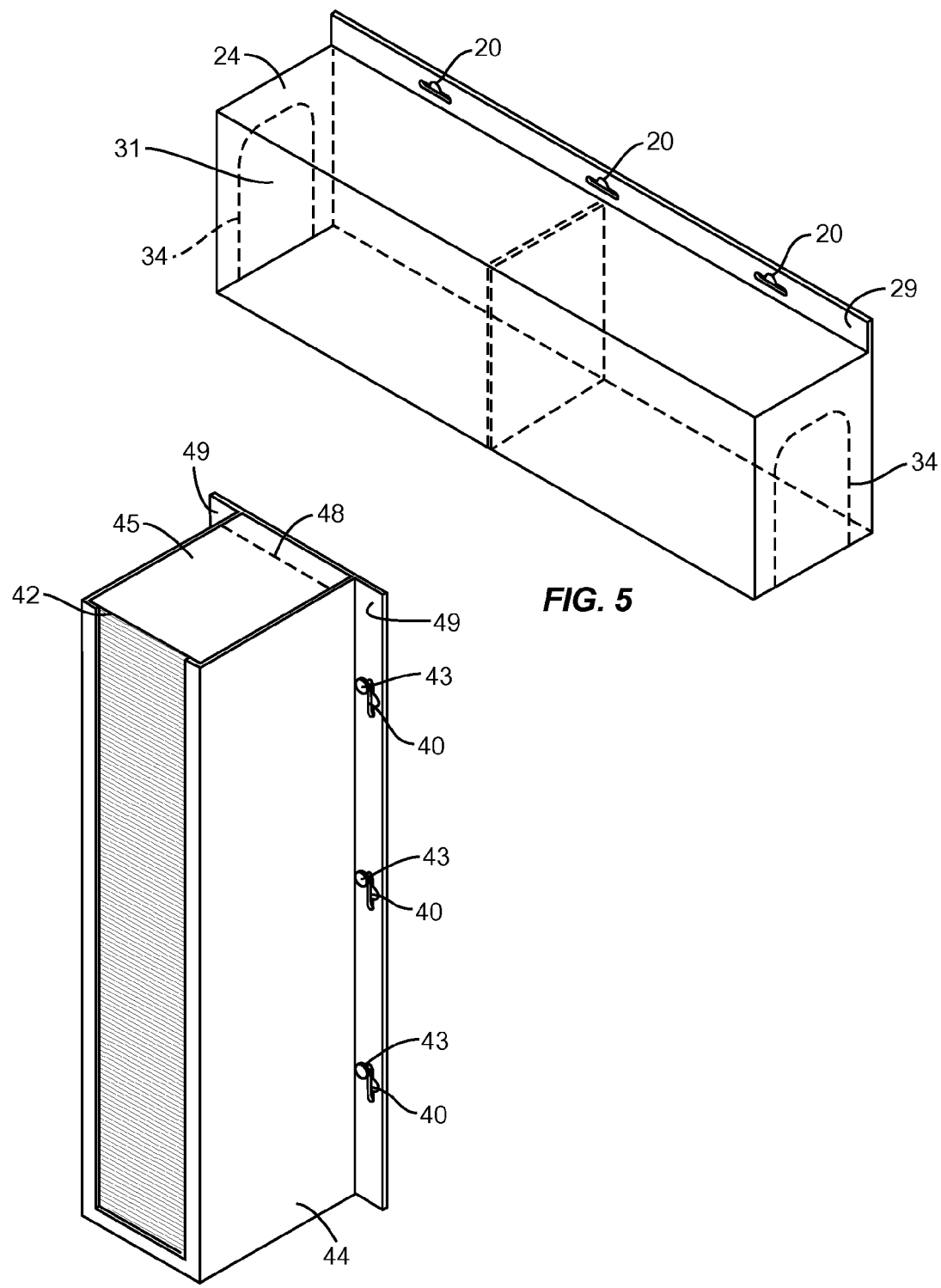
FIG. 5 is a perspective view of the system of FIG. 2 in an unopened state.
FIG. 6 is a perspective view of a system used for storing and dispensing stethoscope covers, mounted in a vertical configuration according to an exemplary embodiment of the present invention.

The enclosure 24 of FIGS. 2 and 3 is shown in FIG. 5 in an unopened state. The enclosure 24 includes two (2) access openings 34 and each access opening 34 encompasses a portion 31. Physicians and/or medical care providers can access covers (not shown) inside the enclosure 24 by tearing away a portion 31 at an access opening 34. The enclosure 24 has a flap 29 including orifices 20 to secure the enclosure 24 to hooks 33 on a mounting bracket 23 that can be mounted on a wall (not shown).

Figure 7:
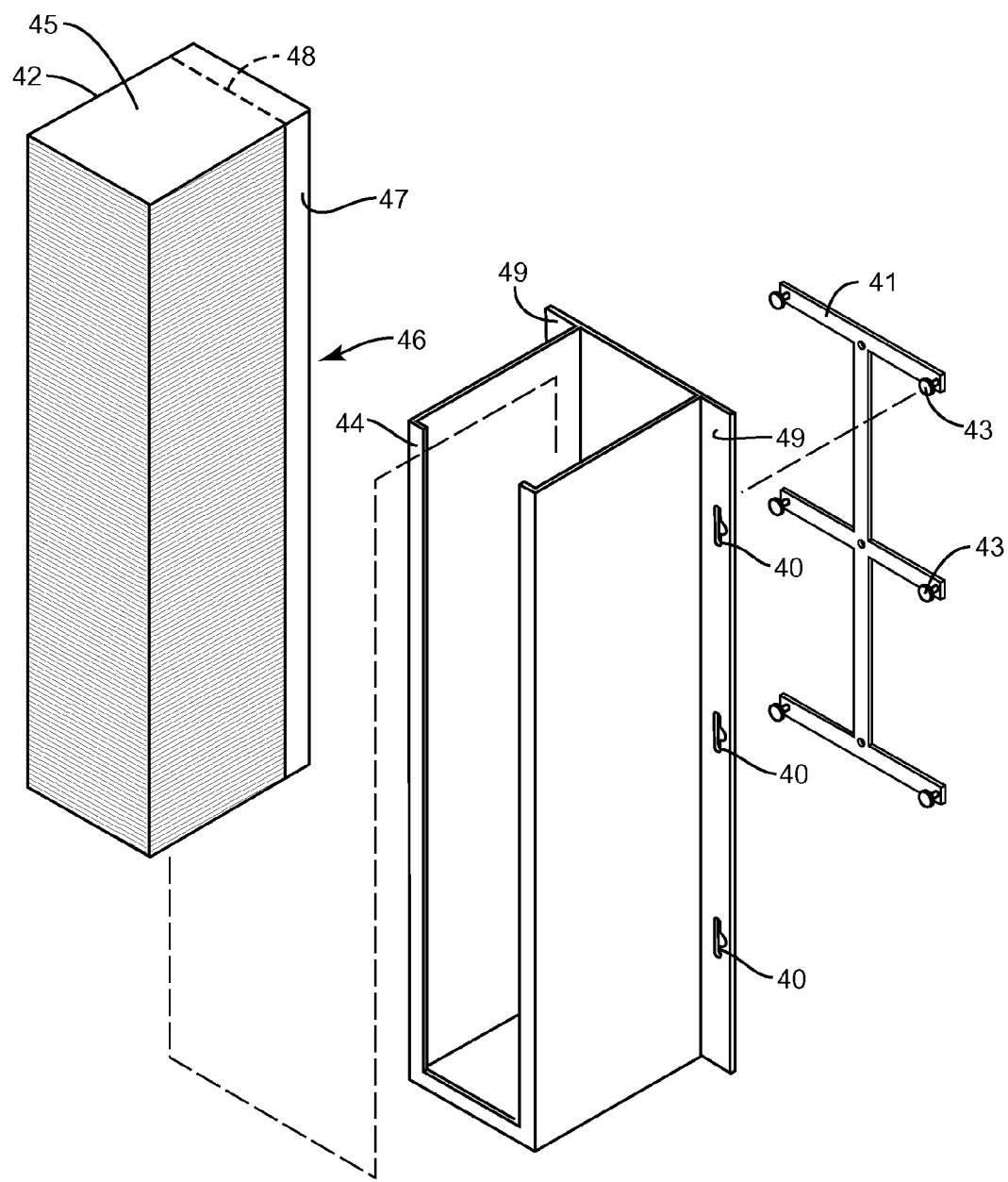
FIG. 7 is an exploded perspective view of the vertically mounted system of FIG. 6.

FIGS. 6 and 7 show an embodiment in which the enclosure 44 is configured to mount in a vertical position. In this embodiment, a flap 49 is configured on opposite sides of the enclosure 44, as opposed to just a single side of the enclosure 44 as described in other embodiments. A modified mounting bracket 41 has hooks 43 to attach to the orifices 40 on each of the flaps 49. The covers 42 in this embodiment are binded together by a binding 47 to form one block 46. The covers 42 include a layer of adherent material 45 and a layer of crimpable material (not shown). The block 46 does not include a central plate. The binding 47 runs the entire length of the enclosure 44 instead of being divided into two parts separate parts by a central plate. Each cover 42 has a line of perforation 48 to allow for easy dislodging of the covers 42 from the binding 47.

With respect to use of the embodiment shown in FIGS. 6 and 7, a medical care provider or user can gently press the diaphragm of a stethoscope (not shown) onto the adherent material layer 45 of a cover 42 facing the opening of the enclosure 44. The cover 42 will thereby form a substantially air-tight seal with the diaphragm of the stethoscope (not shown). The user can then raise the head of the stethoscope (not shown) away from the enclosure 44 and thereby tear or separate the cover 42 from the binding (not shown) at the line of perforation 48. The cover 42 thereby emerges attached to the stethoscope (not shown) with a substantially air-tight seal. The user can then fold the edges of the cover 42 around the head of the stethoscope (not shown) and then crimp the cover 42 around the head of the stethoscope (not shown). To remove the cover 42, the user can simply pull the cover 42 from the stethoscope (not shown).

Figure 8:
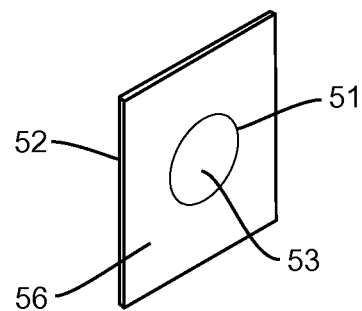
FIG. 8 is a perspective view of a cover for a stethoscope according to another exemplary embodiment of the present invention.
Figure 9:
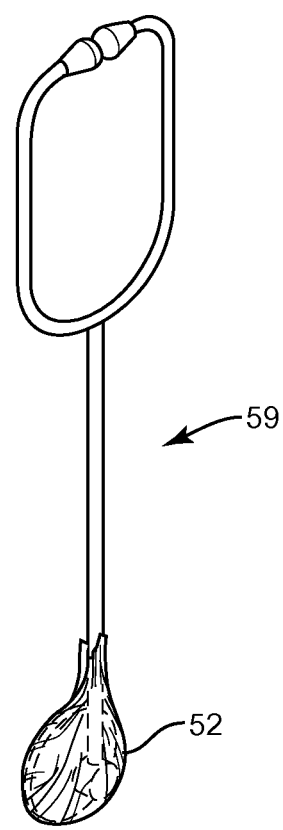
FIG. 9 is a perspective view of the cover of FIG. 8 as adhered onto the diaphragm and head of a stethoscope.

FIG. 8 shows another embodiment of a cover 52. The cover 52 has a first region 51 which has a first side 53 and a second side (not shown). The first side 53 includes an adherent material for removably adhering the first region 51 to the diaphragm of a stethoscope (not shown). The second side (not shown) includes an antimicrobial layer having an antimicrobial substance that can neutralize or destroy microbes disposed thereon. The cover 52 also has a second region 56 configured to be continuous with the first region 51. The second region 56 includes a crimpable material to form-fit around at least the head of the stethoscope (not shown) so as to cover the head of the stethoscope from contamination. The first region 51 is acoustically transmissive and substantially impermeable to microorganisms and fluids. The cover 52 of FIG. 8 is shown in FIG. 9 as adhered onto the diaphragm (not shown) and head (not shown) of a stethoscope 59. The cover 52 is crimped onto the diaphragm (not shown) and head (not shown) of the stethoscope 59.

The covers in various embodiments are disposable. Further, in various embodiments, the covers can have a geometrical shape of a circle, rectangle, octagon, trapezoid, triangle, square or other polygon that is greater than the size of the head of the stethoscope. In one embodiment, the covers are 10 cm×14 cm rectangles. The size of the covers can vary depending on the size of the stethoscope. With respect to the thickness of the covers, in various embodiments, the covers have a thickness in the range of from about 0.01 mm to about 0.8 mm. In some embodiments, the covers have a thickness in the range of from about 0.1 mm to about 0.4 mm.

The covers of the various embodiments do not change the acoustics of a stethoscope and are acoustically transmissive. The covers are substantially impermeable to microorganisms and fluids and will prevent cross-contamination between patients. The various covers can further be used with a variety of medical devices to prevent cross-contamination between patients.

The adherent material in the various embodiments can include one or more of a cellophane, vinyl, acetate, polyethylene acrylic, butyl rubber, ethylene-vinyl acetate, natural rubber, a nitrile, silicone rubber, a styrene block copolymer, a vinyl ether and a tackifier. In some embodiments, the adherent material further includes an antimicrobial and/or antiseptic material. Antiseptic materials that can be used include but are not limited to: alcohols such as ethanol, 1-propanol and 2-propanol/isopropanol or mixtures of these alcohols; sodium bicarbonate; hydrogen peroxide; benzalkonium chloride; chlorohexidine; hexachlorophene; iodine compounds; and combinations thereof. Antimicrobial materials that can be used include but are not limited to: beta-lactam antibiotics (such as penicillin, cephalosporin); protein synthesis inhibitors (such as aminoglycosides, macrolides, tetracycline, chloramphenicol, polypeptides); sulphonamides; cotrimoxazole; quinolones; anti-viral agents; anti-fungal agents; anti-cancer drugs; anti-malarial drugs; anti-tuberculosis drugs; anti-leprotic drugs; anti-protozoal drugs; and combinations thereof. In various embodiments, the antimicrobial material is at least partially removable so that at least a portion of the antimicrobial material is left behind as a cover is removed from a stethoscope.

In various embodiments, the crimpable material includes one or more of polyvinyl chloride, polyvinylidene chloride, low density polyethylene, linear low density polyethylene, polyisobutene, poly[ethylene-vinylacetate] copolymer and lightweight aluminum foil. The crimpable material is acoustically transmissive and will not change the acoustics of a stethoscope. In some embodiments, the crimpable material further includes an adhesive material so as to enhance adhesion of the crimpable material to itself so as to secure a cover to a stethoscope.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A cover for a stethoscope having a head and a diaphragm, comprising:
    a first region including a first side comprising an adherent material for removably adhering the cover to the diaphragm and an opposite second side; and
    a second region that encircles the first region, the second region comprising a crimpable material configured to form-fit around at least the head of the stethoscope so as to protect the head of the stethoscope from contamination.
2. A cover as recited in claim 1, wherein at least one of the first and regions is acoustically transmissive.

3. A cover as recited in claim 1, wherein the second side comprises an antimicrobial substance to neutralize or destroy microbes.
4. A cover as recited in claim 1, wherein the first region has a circular cross-sectional configuration configured to correspond to a cross-section of the diaphragm.
5. A cover as recited in claim 1, wherein the second side and the second region are each free of the adherent material.
6. A cover as recited in claim 1, wherein the second region comprises a chemical agent to prevent the cover from sticking to another cover.
7. A cover as recited in claim 6, wherein the chemical agent is wax.
8. A cover as recited in claim 1, wherein the cover is movable between a first configuration in which the second region is planar and a second configuration in which the second region includes a plurality of folds or ridges.
9. A cover as recited in claim 8, wherein the cover is configured to be maintained in the second configuration after the cover moves from the first configuration to the second configuration.
10. A cover as recited in claim 1, wherein the crimpable material further comprises an adhesive material so as to enhance adhesion of the crimpable material to itself so as to secure the cover to the stethoscope.
11. A system for storing and dispensing at least one cover for a stethoscope having a head and a diaphragm, comprising:
    an enclosure including an inner surface defining a receptacle having at least one opening; and
    a plurality of covers removably attached to the enclosure;
    wherein the covers each comprise (a) a first region including a first side comprising an adherent material for removably adhering the cover to the diaphragm and an opposite second side; and (b) a second region that encircles the first region, the second region comprising a crimpable material configured to form-fit around at least the head of the stethoscope so as to protect the head of the stethoscope from contamination.
12. A system as recited in claim 11, wherein the covers are disposed on a removable backing such that the second sides engage the backing.
13. A system as recited in claim 11, wherein the enclosure comprises a roller mechanism configured to hold the covers, wherein the covers are removably disposed on a releasable backing, the covers being wound about a roller such that the roller advances to expose a next available cover as one of the covers is dispensed from the backing.
14. A system as recited in claim 13, wherein:
    the plurality of covers includes lines of perforations between adjacent covers to allow one of the covers to separate from an adjacent one of the covers; and
    the enclosure further comprises a container for catching the backing after one of the covers is removed from the backing.
15. A system as recited in claim 11, wherein the enclosure further comprises an antimicrobial ultraviolet light source within the receptacle configured to sterilize the covers within the receptacle.
16. A method for covering at least a portion of a stethoscope, comprising:
    engaging a diaphragm of the stethoscope with a first side of a first region of a stethoscope cover, the first side comprising an adherent material for removably adhering the stethoscope cover to the diaphragm; and
    crimping a second region of the stethoscope cover that encircles the first region about a head of the stethoscope such that the second region is form-fit around the head to protect the head from contamination, the second region comprising a crimpable material.

17. A method as recited in claim 16, further comprising:
dispensing the stethoscope cover from an enclosure comprising the stethoscope cover and a plurality of other stethoscope covers before engaging the diaphragm of the stethoscope with the first side, wherein the stethoscope cover and the plurality of other stethoscope covers are disposed on a backing such that the first side of the stethoscope cover is spaced apart from the backing; and
removing the backing from the stethoscope cover before crimping the second region.

18. A method as recited in claim 16, further comprising:
dispensing the stethoscope cover from an enclosure comprising the stethoscope cover and a plurality of other stethoscope covers before engaging the diaphragm of the stethoscope with the first side, wherein the stethoscope cover and the plurality of other stethoscope covers include lines of perforations between adjacent covers; and
removing the stethoscope cover from the plurality of other stethoscope covers by tearing the line of perforation between the stethoscope cover and an adjacent one of the plurality of other stethoscope covers before crimping the second region.

19. A method as recited in claim 16, wherein a second side of the stethoscope cover opposite the first side is free of any adherent material.

20. A method as recited in claim 16, wherein the crimpable material comprises an adhesive material so as to enhance adhesion of the crimpable material to itself so as to secure the cover to the stethoscope.

* * * * *